United States Patent [19]

Smith

[11] 4,286,875
[45] Sep. 1, 1981

[54] DIFFRACTOMETER

[75] Inventor: Francis H. Smith, York, England

[73] Assignee: Vickers Limited, London, England

[21] Appl. No.: 29,125

[22] Filed: Apr. 11, 1979

[30] Foreign Application Priority Data

Apr. 12, 1978 [GB] United Kingdom ............... 14434/78

[51] Int. Cl.³ ............................................ G01N 21/00
[52] U.S. Cl. ..................................... 356/338; 350/89
[58] Field of Search .................... 350/89; 356/336, 338

[56] References Cited

U.S. PATENT DOCUMENTS

| 2,332,668 | 10/1943 | Richards | 350/89 |
| 2,812,686 | 11/1957 | Sinclair | 350/89 X |
| 3,563,660 | 2/1971 | Soloway et al. | 356/336 |

FOREIGN PATENT DOCUMENTS

| 2739274 | 3/1978 | Fed. Rep. of Germany | 350/89 |
| 1130969 | of 0000 | United Kingdom | |
| 1316752 | of 0000 | United Kingdom | |

OTHER PUBLICATIONS

Timbrell "Alignment of Respirable Asbestos Fibres by Magnetic Fields", *Annals. of Occupational Hygiene*, vol. 18, pp. 299-311.

Primary Examiner—John K. Corbin
Assistant Examiner—Matthew W. Koren
Attorney, Agent, or Firm—Browdy and Neimark

[57] ABSTRACT

A diffractometer comprises means for illuminating a specimen plane and a lens for converging rays diffracted from the specimen plane. In order that existing optical apparatus may readily be adapted for use as a diffractometer, the illuminating means (12a, 12b, 13, 14) is arranged to illuminate the specimen plane (0—0') at an acute angle, and a positive lens (15) having its principal axis normal to the specimen plane (0-0') is arranged to converge rays diffracted normally from the specimen plane. The invention is particularly applicable to converting microscopes for use as diffractometers, which then are suitable for use in monitoring respirable airborne fibers.

26 Claims, 1 Drawing Figure

U.S. Patent  Sep. 1, 1981  4,286,875
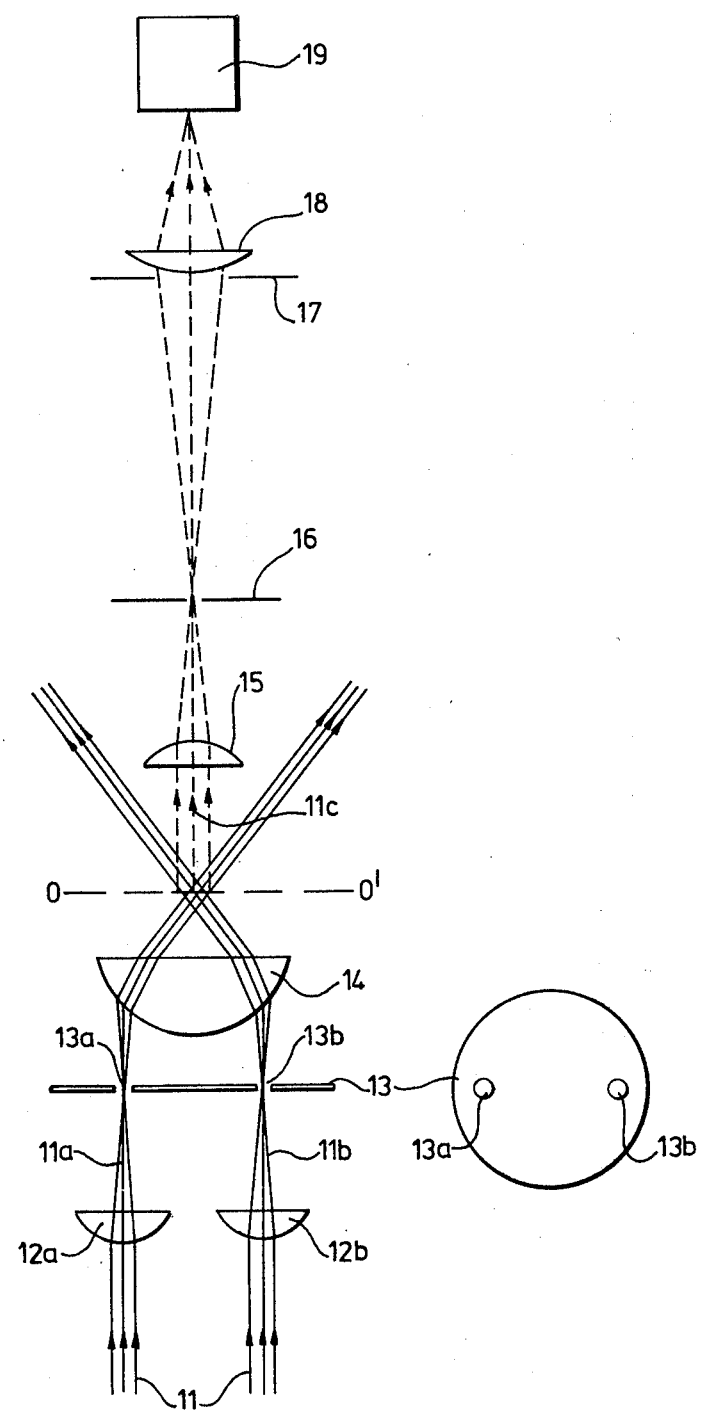

DIFFRACTOMETER

This invention relates to diffractometers, and is particularly although not exclusively concerned with particle counting.

In "Alignment of Respirable Asbestos Fibres by Magnet Fields", published in "Annals of Ocupational Hygiene", Volume 18, pp 299–311, V. Timbrell describes an optical system for monitoring air-borne fiber which have been brought into alignment by application of a magnetic field. Essentially this system is a simple form of diffractometer wherein the light-scattering (diffracting) specimen is illuminated by a normally-incident collimated beam of light and the light which is thereby scattered along a pre-selected path making a specified angle with the incident beam is photo-electrically detected by any appropriate device, e.g. a photo-multiplier.

However, a much more frequently used instrument for respirable particle monitoring is the optical microscope so, in the interests of economy, it would be advantageous to find a convenient way of converting this instrument into a diffractometer as and when required.

Perhaps the most obvious course would be to provide the normally-incident collimated beam by a small illuminated aperature at the units of the microscope condenser's first focal-plane, and thereafter to select the required diffracted beam by a smaller aperture at an appropriate off-axis position at the microscope objective's rear focal plane. Unfortunately, this procedure is impracticable in that microscope objectives having a numerical aperture (NA) sufficient to accept typical preselected angles of diffraction (often as high as 30°) lack the lateral field of view (e.g. 4 mm. diameter) required to sense a statistically significant number of particles.

According to one aspect of the present invention, there is provided a diffractometer comprising means for illuminating a specimen plane at an acute angle thereto, and a positive lens having its principal axis substantially normal to the specimen plane, for converging rays diffracted substantially normally from the specimen plane.

Such a diffractometer may be provided by suitably modifying a microscope (e.g. a photo-electric microscope), and the invention is also concerned with providing means for so modifying a microscope.

According to another aspect of the present invention, there is provided a method of detecting a light-diffracting specimen contained in a specimen plane, the method comprising the steps of illuminating the specimen at an acute angle to the specimen plane, and detecting light diffracted by the specimen normal to the specimen plane.

Such a method may form part of a particle monitoring method as described in the above paper by V. Timbrell, to which paper the reader's attention is directed.

The essence of the present invention consists in exploiting the principle of reversability of optical path. By applying this principle, it can be seen that the intensity of a beam diffracted through, say, 30° from a normal incident beam is the same as that of a normally diffracted beam from an illuminating beam incident at 30°. Thus, a normally diffracted beam can readily be selected by a small aperture at the center of a microscope objective's rear focal-plane, making it possible to use a low-power (and so low NA) objective having a relatively large field of view. The obliquely incident illuminating beam can be formed by an aperture (or apertures) located at an appropriate distance from the center of the first focal-plane of a condenser. Condensers having the necessary NA yet capable of illuminating the required area of a specimen are readily available.

For a better understanding of the invention and to show how the same may be carried into effect, reference will now be made, by way of example, to the accompanying diagrammatic drawings, the single FIGURE of which illustrates an embodiment of the invention.

In the FIGURE, a microscope (e.g. a photo-electric microscope) has been modified to serve as a diffractometer. The modification comprises a substage (optionally removable) which is for illuminating a specimen plane 0–0' and comprises two lenses 12a and 12b, a diaphragm 13, and a condenser 14. Further modifications include an aperture stop 16 and a field stop 17 which need not be removable, but may be so if desired, and an optionally removable photo-detector 19. The microscope may be so modified to serve as a diffractometer as and when required.

An illuminating beam 11 is brought to two foci by the lenses 12a and 12b, which foci are centered on corresponding holes 13a and 13b in the substage diaphragm 13. The substage condenser 14, with its first focal plane at the diaphragm 13, converges the pair of light pencils 11a and 11b formed from the beam 11 onto the specimen plane 0–0' at a pre-selected angle to the normal, defined by the positions of the diametrically opposed holes 13a and 13b. It will be appreciated that this arrangement provides a directional illumination of the specimen plane O–O', and in particular, illumination substantially in one plane. Fibrous specimen particles aligned, say, perpendicularly to the plane of the diagram preferentially diffract the obliquely incident light through a continuous range of angles in planes parallel to the diagram. Dashed lines 11c indicate the normally diffracted portion of this light which is selected by a low power objective lens 15 in association with a central hole in the stop 16 at the rear focal plane of the lens 15. The field stop 17 at the primary image of the illuminated particles formed by the objective 15 serves to restrict the detected area of the specimen and a field lens 18 images the hole in the stop 16 onto the photo cathode of the photo-detector 19.

In order to implement methods as described by Timbrell, it is necessary to provide relative rotation of the specimen relative to the apertures in the diaphragm 13. This is readily achieved by supporting the specimen upon a circular, rotatable stage, as normally provided by conventional polarizing microscopes. Alternatively, it would be possible to rotate the diaphragm 13 together with the associated lenses 12a and 12b (and optionally also the condenser 14), but the former method is presently preferred. In either case, the means for causing the rotation may conveniently comprise an electric motor which can operate continuously to rotate the rotatable stage and/or the diaphragm 13 with associated parts. In carrying out particle counting methods as disclosed by Timbrell, relative rotation between aligned fibers and the illuminating arrangement leads to an output signal from the photodetector 19, which signal has peaks and is indicative of the quantity of fiber in the specimen plane.

It will be understood that provision of the two illuminating beams 11a and 11b is not an essential feature of the invention, as either beam alone would serve. However, there would be a corresponding reduction of signal level at the detector 19, and the resulting asymmetry of illumination might lead to corresponding asymmetry in response relative to specimen versus diaphragm rotation. However, this alternative single beam mode of operation would make one of the lenses 12a and 12b superfluous. As a modification to the illustrated arrangement, each of the apertures 13a and 13b could be in the form of a slot which extends radially of the diaphragm 13, and therefore also radially in relation to the principle axis of the condenser 14. This is because, particularly when the diffractometer is used in methods as described by Timbrell, and possibly also in other applications, the precise angle or angles of incidence of the light on the specimen plane O–O' is not critical. Thus, by allowing a range of a few degrees for the angle of incidence, it is possible to gain a light advantage; i.e., more light is allowed through the diffractometer. For similar reasons, the aperture in the stop 16 could also be in the form of a slot, rather than a circular aperture.

Although the lens 15 is described in the above as a microscope objective lens, it is not essential for the lens 15 to be so. It is merely necessary for the lens 15 to be a positive lens, which acts simply as a collector to converge rays diffracted substantially normally from the specimen plane O–O'.

I claim:

1. A diffractometer comprising means for illuminating a specimen plane at an acute angle thereto, the axis of the or each beam of illuminating light rays lying substantially in a common plane, and a positive lens having its principal axis substantially normal to the specimen plane, for converging rays diffracted substantially normally from the specimen plane.

2. A diffractometer according to claim 1, wherein the illuminating means comprises a condenser arranged to receive a light beam substantially normal to the specimen plane and transmit the light beam across the specimen plane at said angle thereto.

3. A diffractometer according to claim 2, wherein the illuminating means comprises a diaphragm upstream of the condenser, the diaphragm being formed with at least one aperture offset from the principal axis of the condenser, for transmitting to the condenser a light beam which, after exit from the condenser, crosses the specimen plane at said angle thereto.

4. A diffractometer according to claim 3, wherein the diaphragm is formed with two apertures diametrically opposed about the principal axis of the condenser, for transmitting to the condenser two respective light beams which, after exit from the condenser, cross the specimen plane at said angle thereto.

5. A diffractometer according to claim 3, wherein each said aperture is in the form of a slot which extends radially in relation to the principal axis of the condenser.

6. A diffractometer according to claim 3, wherein the illuminating means comprises, upstream of the diaphragm, a respective lens for converging a light beam to a focus at the or each respective said aperture.

7. A diffractometer according to claim 3, including a photo-electric detection means for detecting light from said positive lens.

8. A diffractometer according to claim 2, including a field lens for directing the light from said positive lens onto the photo-electric detection means.

9. A diffractometer according to claim 8, wherein the photo-electric detection means is removable from the diffractometer as desired.

10. A diffractometer according to claim 9, wherein the photo-electric detector and said positive lens form part of a modular assembly which is removable from the diffractometer as desired.

11. A diffractometer according to claim 3, including a field stop for restricting the light which is converged by said positive lens.

12. A diffractometer according to claim 3, including an aperture stop downstream of said positive lens, for limiting the light rays converged by said positive lens to those diffracted substantially normally to the specimen plane.

13. A diffractometer according to claim 3, including means for providing relative rotation between a specimen in the specimen plane and the illuminating means, about the principal axis of said positive lens.

14. A diffractometer according to claim 2, being a microscope selectively convertible for use either as a microscope or as a diffractometer.

15. A diffractometer according to claim 14, comprising a rotatable nosepiece and first and second objective assemblies mounted thereon, which assemblies can be selectively positioned to view the specimen plane, such that the diffractometer may be used as a microscope and a diffractometer respectively, said positive lens forming part of said second assembly.

16. A diffractometer according to claim 14, wherein the illuminating means comprises a modular assembly which is removable from the diffractometer as desired.

17. A method of detecting a light diffracting specimen contained in a specimen plane, said specimen comprising asbestos fibers, the method comprising bringing said fibers into alignment by application of a magnetic field, illuminating the specimen at an acute angle to the specimen plane, and detecting light diffracted by the specimen normal to the specimen plane, wherein the specimen is illuminated and the diffracted light is detected by means 2–16 of a diffractometer according to any one of claims 1 to 3.

18. A method of detecting a light-diffracting specimen contained in a specimen plane, the method comprising the steps of illuminating the specimen at an acute angle to the specimen plane, the axis of the or each beam of illuminating light rays lying substantially in a common plane, and detecting light diffracted by the specimen normal to the specimen plane.

19. A method according to claim 18, wherein the specimen comprises fibers.

20. A method according to claim 19, wherein the fibers are air-borne respirable fibers.

21. A method according to claim 20, wherein said fibers are asbestos fibers.

22. A method according to claim 19, wherein said fibers are brought into alignment by application of a magnetic field.

23. A method according to claim 22, wherein said fibers are asbestos fibers.

24. A method according to claim 22, including the step of obtaining an electrical signal indicative of the quantity of fiber present in the area of the specimen plane detected by the diffractometer.

25. A method according to claim 24, wherein said fibers are asbestos fibers.

26. A method according to claim 19, wherein said fibers are asbestos fibers.

* * * * *